US008492081B2

(12) United States Patent
Nichols et al.

(10) Patent No.: US 8,492,081 B2
(45) Date of Patent: *Jul. 23, 2013

(54) ALDEHYDE-FIXED, DRIED PLATELETS WITH COVALENTLY ATTACHED EXOGENOUS ACTIVE AGENT AND METHOD OF MAKING THEREOF

(75) Inventors: Timothy C. Nichols, Chapel Hill, NC (US); Thomas Fischer, Hillsborough, NC (US); Marjorie S. Read, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1608 days.

This patent is subject to a terminal disclaimer.

(21) Appl. No.: 11/863,462

(22) Filed: Sep. 28, 2007

(65) Prior Publication Data

US 2012/0128647 A1 May 24, 2012

Related U.S. Application Data

(63) Continuation of application No. 10/845,045, filed on May 13, 2004, now Pat. No. 7,294,455.

(60) Provisional application No. 60/533,059, filed on Dec. 29, 2003, provisional application No. 60/471,005, filed on May 16, 2003.

(51) Int. Cl.
*A01N 1/02* (2006.01)
*A01N 63/00* (2006.01)

(52) U.S. Cl.
USPC ............................................ 435/2; 424/93.72

(58) Field of Classification Search
None
See application file for complete search history.

(56) References Cited

U.S. PATENT DOCUMENTS

| | | | |
|---|---|---|---|
| 5,651,966 | A | 7/1997 | Read et al. |
| 5,891,393 | A | 4/1999 | Read et al. |
| 5,902,608 | A | 5/1999 | Read et al. |
| 5,993,804 | A | 11/1999 | Read et al. |
| 6,884,573 | B2 | 4/2005 | Fischer et al. |
| 7,294,455 | B2 * | 11/2007 | Nichols et al. ............... 435/2 |
| 2002/0009500 | A1 | 1/2002 | Wolkers et al. |
| 2002/0114791 | A1 | 8/2002 | Crowe et al. |
| 2003/0054330 | A1 | 3/2003 | Fischer et al. |
| 2006/0270030 | A1 | 11/2006 | Voigt et al. |

FOREIGN PATENT DOCUMENTS

| | | |
|---|---|---|
| JP | 05126696 A | 4/1993 |
| JP | 08-109142 | 4/1996 |
| JP | 2001333771 A | 12/2001 |
| WO | WO 93/23997 A1 | 12/1993 |
| WO | WO 96/32969 | 10/1996 |
| WO | WO 99/24044 | 5/1999 |
| WO | WO 99/34680 A1 | 7/1999 |
| WO | WO 99/55346 | 11/1999 |

OTHER PUBLICATIONS

Merricks et al., "Binding and internalization of fibrinogen and F-actin distribution in rehydrated, lyophilized platelets," Blood 92(10) Supp. 1, part 1-2, 71B (1998).
Sanders, Jr. et al., "Fibrinogen Binding to Rehydrated Lyophilize(d) Platelet Surface GpIIb-IIIa: Normal Clot Formation and TPA Lysis," Blood 88(10) Supp. 1, part 1-2 30A (1988).
Arroyo et al.; In Vivo Photoactivation of Caged-Thrombin *Thromb Haemost* 78 791-793 (1997).
Artemov, Dmitri; "Molecular Magnetic Resonance Imaging with Targeted Contrast Agents" *Journal of Cellular Biochemistry* 90 518-524 (2003).
Bode et al.; "Activation and adherence of lyophilized human platelets on canine vessel strips in the Baumgartner perfusion chamber" *J. Lab. Clin. Med.* 133:2 200-211 (1999).
Chaterjee et al.; "Size dependent magnetic properties of iron oxide nanoparticles" *Journal of Magnetism and Magnetic Materials* 257 113-118 (2003).
Chu et al.; "Derivatization of unprotected polynucleotides" *Nucleic Acids Research* 11:18 6513-6529 (1983).
Crotty et al.; "Ribavirin's antiviral mechanism of action; lethal mutagenesis?" *J. Mol. Med.* 80 86-95 (2002).
DiStefano et al.; "Liver Glycotargeting of Antiviral Nucleoside Analogues" *Trends in Glycosci. and Glycotech.* 50 461-472 (1997).
Douri et al.; "Effect of the administration of recombinant activated factor VII (rFVIIa; NovoSeven®) in the management of severe uncontrolled bleeding in patients undergoing heart valve replacement surgery" *Blood Coagulation and Fibrinolysis* 11:supp 1 S121-S127 (2000).
Dutton et al.; "Recombinant Factor VIIa for Control of Hemorrhage: Early Experience in Critically Ill Trauma Patients" *Journal of Clinical Anesthesia* 15 184-188 (2003).
Fischer et al.; "Intracellular function in rehydrated lyophilized platelets" *British Journal of Haematology* 111 167-174 (2000).
Fischer et al.; "Splenic Clearance Mechanisms of Rehydrated, Lyophilized Platelets" *Art. Cells, Blood Subs., and Immob. Biotech.* 29:6 439-451 (2001).
Flacke et al.; "Novel MRI Contrast Agent for Molecular Imaging of Fibrin Implications for Detecting Vulnerable Plaques" *Circulation* 104 1280-1285 (2001).
Hedner et al.; "Management of Hemophilia Patients with Inhibitors" *Hematology/Oncology Clinics of North America* 6:5 1035-1046 (1992).
Kristensen et al.; "Clinical Experience with Recombinant Factor VIIa in Patients with Thrombocytopenia" *Haemostasis* 26:supp. 1 159-164 (1996).
Monahan et al.; "Adeno-associated virus vectors for gene therapy: more pros than cons?" *Molecular Medicine Today* 6 433-440 (2000).
Monroe at al.; "Platelet activity of high-dose factor VIIa is independent of tissue factor" *British Journal of Haematology* 99 542-547 (1997).
Monroe et al.; "The Factor VII-Platelet Interplay: Effectiveness of Recombinant Factor VIIa in the Treatment of Bleeding in Severe Thrombocytopathia" *Seminars in Thrombosis and Hemostasis* 26:4 (2000).
Nichols et al.; "Porcine von Willebrand Disease and Atherosclerosis" *American Journal of Pathology* 140:2 403-415 (1992).
Pankhurst et al.; "Applications of magnetic nanoparticles in biomedicine" *Journal of Physics D: Applied Physics* 36 R167-R181 (2003).
Poon et al.; "Recombinant activated factor VII (NovoSeven®) treatment of platelet-related bleeding disorders" *Blood Coagulation and Fibrinolysis* 11:supp 1 S55-S68 (2000).

(Continued)

*Primary Examiner* — Sandra Saucier
(74) *Attorney, Agent, or Firm* — Myers Bigel Sibley & Sajovec, P.A.

(57) ABSTRACT

Fixed-dried blood cells carrying an active agent are described, along with methods of making the same, methods of using the same, and compositions containing the same. The blood cells are preferably blood platelets.

35 Claims, 6 Drawing Sheets

OTHER PUBLICATIONS

Read et al.; "Preservation of hemostatic and structural properties of rehydrated lyophilized platelets: Potential for long-term storage of dried platelets for transfusion" *Proc. Natl. Acad. Sci.* USA 92 397-401 (1995).

Rofsky et al.; "MR Angiography in the Evaluation of Atherosclerotic Peripheral Vascular Disease" *Radiology* 214:2 325-338 (2000).

Khandelwal et al.; "von Willebrand Factor Binding to Rehydrated Lyophilized Platelet Surface GPIb and Inhibition by Monoclonal Antibody to GPIb" *Abstract Only*. The FASEB Journal, 11, abstract #1812, p. A312 (1997).

Fraternale et al. Macrophage protection by addition of glutathione (GSH)-loaded erythrocytes to AZT and DDI in a murine AIDS model. Antiviral Research. 2002, vol. 56, pp. 263-272.

"Notification of the Transmittal of the International Search Report and the Written Opinion of the International Searching Authority, or the Declaration" For International Application No. PCT/US04/15320, mailed Oct. 28, 2005.

Campbell et al. "A Novel Use of Rehydrated, Lyophilized Platelets Increases Recombinant FvIIa Procoagulant Activity in a Model of Hemophilia" *Blood* 108(11) (p. 1 of 2) (Abstract Only) (2006) and *48th Annual Meeting of the American Society of Hematology*, Orlando, FL, USA (2006).

Fraternale et al. "Role of Macrophage Protection on the Development of Murine AIDS" *JAIDS Journal of Acquired Immune Deficiency Syndromes* 21:81-89 (1999).

Supplemental European Search Report for Application No. PCT/US2004015320; dated May 29, 2007.

Examiner's First Report on Patent Application AU 2004269308, IP Australia, Nov. 6, 2008, 3 pages.

Examination Report, EP 04 801 949.1, European Patent Office, Nov. 13, 2008, 6 pp.

Freitas RA, Jr. Amorphous carbon particles. Nanomedicine, vol. IIA: Biocompatibility. Landes Bioscience, Georgetown, TX. 2003, Section 15.3.3.5, 6 pages.

* cited by examiner

Flow cytometric analysis of rFVIIa-FITC bound to RL platelets

Examples:

Sample # 1d
10 uM total rFVIIa
$3 \times 10^4$ RL platelets/ul

Sample # 2a
3 uM total rFVIIa
$9 \times 10^5$ RL platelets/ul

US 8,492,081 B2

ALDEHYDE-FIXED, DRIED PLATELETS WITH COVALENTLY ATTACHED EXOGENOUS ACTIVE AGENT AND METHOD OF MAKING THEREOF

RELATED APPLICATIONS

This application is a continuation of U.S. patent application Ser. No. 10/845,045, filed May 13, 2004, now U.S. Pat. No. 7,294,455 and claims the benefit of U.S. Provisional Patent Application Ser. No. 60/533,059, filed Dec. 29, 2003, and U.S. Provisional Patent Application Ser. No. 60/471,005, filed May 16, 2003, the disclosures of which are incorporated by reference herein in their entirety.

This application is also related to U.S. patent application Ser. No. 11/751,295, filed May 21, 2007; and U.S. patent application Ser. No. 11/149,515, filed Jun. 10, 2005; which are divisional and continuation applications, respectively, of application Ser. No. 10/845,045; the disclosures of which are incorporated by reference herein in their entirety.

STATEMENT OF GOVERNMENT SUPPORT

This invention was made with government support from the Department of Defense and the National Institutes of Health under Grant Numbers 1-P20-DE123474, 1-P60-DE 130789, and 1 R21 EB002863, and with government support from the Office of Naval Research under Grant Numbers N00014-97-1-0867 and N00014-97-1-0891. The United States Government has certain rights to this invention.

FIELD OF THE INVENTION

The present invention concerns methods and compositions for delivering active agents to a subject in need thereof and more particularly to fixed-dried blood cells that carry an active agent and that are useful to deliver active agents to a site of interest.

BACKGROUND OF THE INVENTION

Platelets have been recognized for decades as potential tools for carrying therapeutics to sites of vascular injury. However, the practical utility of platelets as therapeutic delivery vehicles has been limited because platelets must be freshly isolated, modified with the therapeutic, and then infused in a short time-span. The utility of cryopreserved platelets and normally liquid-stored for therapeutic delivery is limited by storage lesion and, in the case of frozen platelets, the need to remove cryopreservatives. Hence the practical application of cryopreserved platelets, as well as preserved blood cells in general, has been limited.

SUMMARY OF THE INVENTION

A first aspect of the present invention is fixed-dried blood platelets, red blood cells (RBCs,) or combinations thereof carrying a heterologous compound, active agent or compound of interest, along with compositions comprising, consisting of or consisting essentially of the same. Such platelets, RBCs or combinations thereof are preferably mammalian blood cells such as human blood platelets and RBCs. The compound or active agent may be associated with the platelets and/or RBCs in any manner, such as coupling by or being contained within the platelets and/or RBCs. The platelets and/or RBCs may be aldehyde-fixed, and in one embodiment the platelets are characterized in that they adhere to thrombogenic surfaces; undergo shape change upon adhering to a thrombogenic surface; lead to the formation of a hemostatic plug upon adhering to a thrombogenic surface; and release their granular contents. The active agent or compound to be delivered may be an antiviral agent such as a nucleoside analog antiviral agent (for example ribavirin), a blood coagulation protein such as Factor VII, a nucleic acid (e.g., DNA, RNA), a detectable compound such as a detectable protein or peptide, etc.

A second aspect of the present invention is a pharmaceutical composition comprising, consisting of or consisting essentially of, for example, from 0.01 or 0.1 to 99.9 or 99.99 percent by weight of a pharmaceutically acceptable carrier (e.g., an aqueous or nonaqueous carrier; a solid, liquid or gel carrier, etc.); and, for example, from 0.01 or 0.1 to 99.9 or 99.99 percent by weight of fixed-dried blood cells carrying an active agent as described herein, the fixed-dried blood cells optionally rehydrated in the pharmaceutically acceptable carrier.

A further aspect of the present invention is a method of making fixed-dried blood cells for delivering a compound of interest or an active agent to a subject in need thereof, comprising: providing fixed blood cells (typically mammalian cells and preferably human cells, particularly RBCs, platelets, and combinations thereof) carrying the active agent; associating the active agent to the fixed blood cells; and drying the fixed blood cells (e.g., by freeze-drying or lyophilization) to produced fixed-dried blood cells carrying the active compound. The method may further comprise the step of rehydrating the fixed-dried blood cells in a pharmaceutically acceptable carrier to provide a pharmaceutically acceptable composition comprising rehydrated fixed-dried blood cells carrying the active agent. The associating step may be carried out by any suitable means, such as by coupling the active agent to the cells or introducing the active agent into the cells. The cells may be aldehyde-fixed platelets, and in one embodiment the cells are platelets that are characterized in that, upon reconstitution, they: adhere to thrombogenic surfaces; undergo shape change upon adhering to a thrombogenic surface; lead to the formation of a hemostatic plug upon adhering to a thrombogenic surface; and release their granular contents.

A further aspect of the present invention is a method of delivering a compound of interest to a thrombogenic surface (e.g., in a subject, or to a tissue in vitro for diagnostic or compound testing purposes), comprising: providing fixed-dried blood cells carrying the compound of interest as described herein; rehydrating the fixed-dried blood cells in an acceptable carrier (e.g., a pharmaceutically or physiologically acceptable carrier) to provide a composition comprising rehydrated fixed-dried blood cells carrying the active agent; and then administering the pharmaceutical composition (e.g., to the subject, to the tissue in vitro) so that an effective amount of the compound of interest is delivered to a thrombogenic surface. The subject is typically a mammalian subject such as a human subject, and the compound of interest may be a diagnostic or therapeutic agent.

A further aspect of the present invention is a method of delivering a compound of interest to macrophages of the RES in a subject. The subject is typically a mammalian subject such as a human subject, and the compound of interest may be a diagnostic or therapeutic agent.

A further aspect of the present invention is a method of delivering an active agent to a site of interest (e.g., to a subject or to a tissue in vitro), comprising: providing fixed-dried blood cells carrying the active agent as described herein; rehydrating the fixed-dried blood cells in a pharmaceutically acceptable carrier to provide a pharmaceutically acceptable composition comprising rehydrated fixed-dried blood cells carrying the active agent; and then administering the pharmaceutical composition to the site of interest (e.g., to a subject or to a tissue in vitro), so that an effective amount of the active agent is delivered to said site of interest. The effective amount of active agent may be less than 15% (15 percent) of endogenous platelet equivalent. The subject is typically a mammalian subject such as a human subject, and the active agent may be a diagnostic or therapeutic agent. The cells may be aldehyde-fixed cells, and the subject may for example be afflicted with a vascular injury.

The foregoing and other objects and aspects of the present invention are explained in greater detail below.

DETAILED DESCRIPTION OF THE PREFERRED EMBODIMENTS

Figure 1:
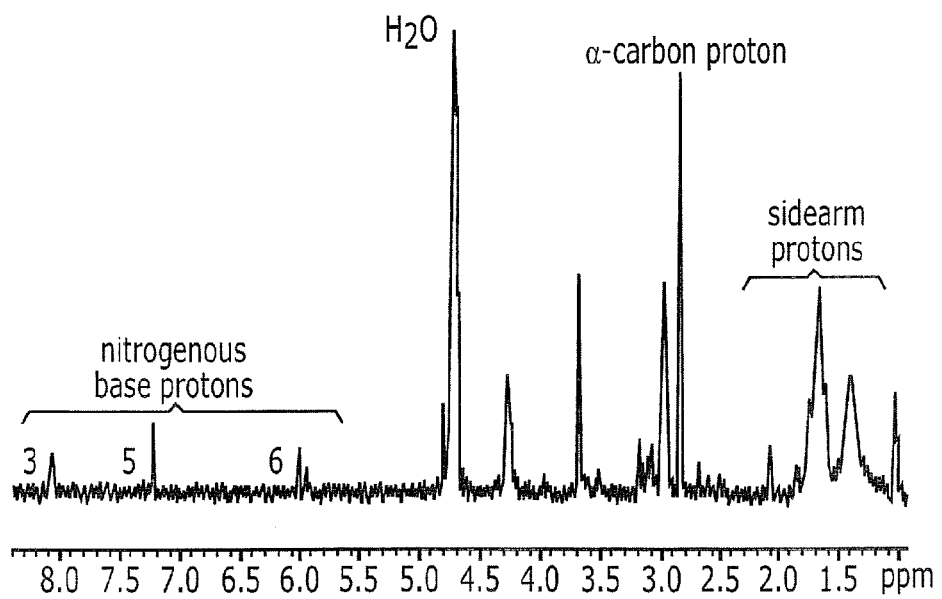
FIG. 1 shows the proton NMR Spectra of nucleoside copolymers.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Subjects to be treated with the methods and compositions of the present invention include both human subjects and animal subjects for veterinary and drug development purposes. Animal subjects are, in general, mammalian subjects, including but not limited to pig, sheep, cow, horse, goat, cat, dog, mouse and rat subjects.

"Thrombogenic surface" as used herein refers to any natural or artificial thrombogenic surface, including but not limited to wound tissue, blood vessel plaques such as atherosclerotic plaques, activated endothelium due to local or systemic inflammation, vessels, surfaces or tissues that are rendered thrombogenic in a subject as a toxic side-effect due to administration of anticancer, antineoplastic or antiproliferative agent, surfaces of foreign or implanted items in the subject, including metals, polymers, etc., as found in stents, catheters, biomedical implants such as pacemakers and leads, orthopedic implants such as artificial joints, etc. A compound may be administered to a thrombogenic surface for any purpose, such as for therapeutic purposes or diagnostic purposes (e.g., imaging or detection of a thrombogenic surface by any suitable means such as radioimaging, tissue biopsy, implant removal and determination of whether the delivered compound is found on the implant surface, etc.).

"Platelets" utilized in carrying out the present invention are, in general, of animal, and preferably mammalian, origin (e.g., pig, sheep, cow, horse, goat, cat, dog, mouse, rat, human, etc.). Platelets may be derived from the same species into which the platelets are introduced, or from a different species from which the platelets are introduced. In one embodiment, platelets are harvested from a subject, used to prepare the active agents described herein, and after being so prepared are administered at a later time back to the same subject from which the platelets were harvested.

"Red blood cell" as used herein includes any erythrocyte of mammalian origin (e.g., pig, sheep, cow, horse, goat, cat, dog, mouse, rat, human, etc.). Red blood cells may be derived from the same species into which the red blood cells are introduced, or from a different species from which the red blood cells are introduced. In one embodiment, red blood cells are harvested from a subject, used to prepare the active agents described herein, and after being so prepared are administered at a later time back to the same subject from which the red blood cells were harvested.

"Fixed blood cells" herein refers to blood cells, which may be platelets, red blood cells, or mixtures thereof, which have been chemically treated with at least one chemical compound that is incorporated into at least a portion of the cells to structurally stabilize and/or extend the shelf-life of the cells.

"Fixed-dried blood cells" herein refers to blood cells, which may be platelets, red blood cells, or mixtures thereof, which have been fixed, and additionally have had water removed therefrom by any suitable technique such as drying, dehydrating, lyophilizing or freeze-drying, etc., to further structurally stabilize and/or extend the shelf-life thereof.

"Rehydrated fixed-dried blood cells" refers to a fixed-dried blood cells, which may be platelets, red blood cells, or mixtures thereof, which has been contacted to or combined with an aqueous solution so that water is taken up into the intracellular space.

"Blood coagulation protein" as used herein includes any suitable blood coagulation protein, including but not limited to Factor VII, Factor IX, Factor X, as well as coagulation proteins that generate Factor VII or FVIIa, such as Factor XII or Factor XIIa, or Factor X or Factor Xa, Protein C, Protein S, and Prothrombin. Such proteins may be natural or synthetic and include proteins containing minor modifications of the naturally occurring protein (i.e., analogs). Where naturally occurring the protein may be of any species of origin, preferably mammalian or human as described herein, and in one embodiment is of the same species of origin as the subject to which it is administered.

"Blood anti-coagulation protein" as used herein includes any suitable blood anti-coagulation protein, including but not limited to activated protein C, protein S, heparin and heparinoids, etc. Such proteins may be natural or synthetic and include proteins containing minor modifications of the naturally occurring protein (i.e., analogs). Where naturally occurring the protein may be of any species of origin, preferably mammalian or human as described herein, and in one embodiment is of the same species of origin as the subject to which it is administered.

"AAV" as used herein refers to "adeno-associated virus".

The term "treat" as used herein refers to any type of treatment that imparts a benefit to a patient afflicted with a disease, including improvement in the condition of the patient (e.g., in one or more symptoms), delay in the progression of the disease, etc.

The term "pharmaceutically acceptable" as used herein means that the compound or composition is suitable for administration to a subject to achieve the treatments described herein, without unduly deleterious side effects in light of the severity of the disease and necessity of the treatment.

Applicants specifically intend that the disclosures of all United States patent references cited herein be incorporated by reference herein in their entireties.

1. Platelets.

Platelets may be fixed in accordance with known techniques, such as described in U.S. Pat. Nos. 4,287,087; 5,651,966; 5,902,608; 5,891,393; and 5,993,084. In general, such methods involve providing blood platelets (e.g., human, mammalian); contacting said human platelets to a fixative (e.g., an aldehyde) for a time sufficient to fix said platelets; removing said fixative from said platelets; and then drying said platelets to produce fixed-dried blood platelets. In a preferred embodiment, the contacting step is carried out for a time sufficient to kill said microorganisms. In a preferred embodiment, the contacting step is carried out for a time insufficient to cause said platelets to lose the capability, upon reconstitution, to; (i) adhere to thrombogenic surfaces; (ii) not adhere to non-thrombogenic surfaces; (iii) undergo shape change (spreading) upon adhering to a thrombogenic surface; (iv) adhere to one another to form a hemostatic plug upon adhering to a thrombogenic surface; and (v) release their granular contents.

More particularly, fixed-dried blood platelets for use in the present invention may be fixed with a compound selected from the group consisting of formaldehyde, paraformaldehyde and glutaraldehyde, with paraformaldehyde currently preferred. In general, washed platelets may be fixed by incubating them, typically at room temperature, for up to 60 minutes in a solution of up to 1.8% aldehyde. An alternative technique is to fix platelets by incubating the platelets in a permanganate solution (e.g., sodium permanganate, potassium permanganate). In general, washed platelets may be prepared by this technique by incubating them for from 5 to 20 minutes in from 0.001 to 1 g/dL of $KMnO_4$ or $NaMnO_4$ solution, more preferably by incubating them for from 5 to 15 minutes in from 0.005 to 0.5 g/dL of $KMnO_4$ or $NaMnO_4$ solution, Blood platelet preparations for use in preparing pharmaceutical formulations should be essentially free of extraneous matter, particularly lysed blood platelets which would present free thrombogenic agents to a patient administered the preparation. Hence, care must be taken to sufficiently fix the platelets (preferably without destroying the viability thereof, as indicated by the characteristics set forth above) prior to drying, as undue lysis will otherwise occur during the drying step. For example, platelet preparations suitable for use in preparing human pharmaceutical formulations preferably show, on reconstitution of $10^9$ platelets in one milliliter of solution, less than $10 \times 10^6$ microparticles (the fragmentary remains of lysed platelets) per milliliter, and preferably show less than 150 International Units (IU) per liter of lactate dehydrogenase in the supernatant after resuspension and pelleting (where 2200 IU per liter represents total lysis of $10^9$ cells in 1 milliliter).

Drying of platelets after fixation may be carried out by any suitable means, but is preferably carried out by lyophilization. Care should be taken to stabilize the platelet preparation prior to drying as an unacceptable level of platelet lysis may otherwise occur. Stabilization may be carried out by suspending the platelets in a solution containing a suitable water replacing molecule (or "stabilizer"), such as albumin or trehalose, and then drying the solution. In one embodiment, from 0.1 to 20 percent by weight albumin is employed, more preferably from 1 to 10 percent by weight albumin is employed, and most preferably from 5 to 10 percent by weight albumin is employed. For administration to a subject, the albumin in the preparation should be of the same species as the subject (e.g., human albumin). In the alternative, the preparation may be dried with albumin of a different species, the albumin separated from the platelets on reconstitution, and albumin of the same species added back to the reconstituted preparation for administration to the subject, but care should be taken to remove all non-species specific albumin as it may be antigenic in the subject being treated. Once dried, the platelets may be coupled or associated with a compound to be delivered to produce an "active agent" of the present invention, as described further below.

2. Lyophilized RBCs.

Cross-linked and lyophilized RBCs of the present invention may be prepared with bifunctional cross-linking reagents that are homo or heteromeric with reactive the following reactive moieties: aldehydes, ketones, hydrazides, N-hydroxysulfosuccinimides, N-hydroxysuccinimides, maleimides, imidoesters, active halogens, pyridyl-disulfides, isocyanates, nitrobenzoyloxysuccinimides, nitrobenzenes, imidoesters, photo-activatable azidophenyls and azidopolyaromatics, as well as zero-spacer carbodimide catalysts. Multi (poly) functional reagents are also considered, as are combinations of two or more cross-linkers, either serially reacted with RBCs for reacted together with RBCs.

RBCs are obtained from mammalian blood with standard phlebotomy, apheresis or exsanguination methods according to approved IACCOC protocols. RBCs are freed from plasma platelets, leukocytes and plasma proteins my differential centrifugation, and then treated with chemical cross-linkers. The reaction of the RBCs with the cross-linkers are in general carried out for defined periods of time at temperatures between 20° C. and 37° C. at pre-determined concentration of RBCs. As discussed in greater detail below, care must be taken to sufficiently fix the platelets or undue lysis will be measured upon rehydration of the lyophilized product. The cross-linking step can be carried out in the presence of anti-oxidants and free-radical scavengers, and the cross-linking reaction can be quenched by adding compounds that contain primary amines. After cross-linking, the RBCs are removed from excess cross-linker and reaction products with differential centrifugation, chromatography and/or dialysis.

Freezing of RBCs after cross-linking may be carried out over a wide range of cooling rates at ambient or hyperbaric pressures. If RBCs (with zero or reduced concentrations of cross-linkers) are frozen into the high-pressure phase states of ice (e.g., ice II/III) samples are preferably isothermally pressurized and then isobarically cooled to under −120° C., the point at which ice II/III is metastable. RBCs can be frozen in the presence of "stabilizer" small molecules (e.g., glycerol), proteins (e.g., albumin) and polymers (e.g., PEG) which substitute for water in the ice crystal matrix. The preferred "stabilizer" is PEG 8,000 at a final concentration of 1% (w.v). The type and level of "stabilizer" must be infusible as rehydrated. Lyophilization is carried out from temperatures below 0° C., preferably 40° C. if the RBCs were frozen at ambient pressure for ice I, and near or less than −120° C. for molecular distillation from the ice II/III phase states.

The chemical modification of RBC membranes with cross-linkers imparts a "foreign" nature to the cells with respect to recognition by the reticuloendothelial system and thrombogenic with respect to contact activation of platelets. The surface membrane is thus occluded by covalently attaching polymers that sterically coat the cell membrane. Polymers, particularly water-soluble polymers, that may be used to carry out the present invention are, in general, naturally occurring polymers such as polysaccharides, or synthetic polymers such as polyalkylene oxides such as polyethylene glycols (PEG), polyalkylene glycols, polyoxyethylated polyols, polyvinylpyrrolidone, polyacrylates such as polyhydroxyethyl methacrylate, polyvinyl alcohols, and polyurethane. The polymers may be linear, branched or dendrimeric and may be substituted or unsubstituted. The polymers may, as noted above, be hydrophilic, lipophilic, or both hydrophilic and lipophilic. Polymers are covalently attached through the membrane through reactive chemical functions that include, but are not limited to, aldehydes, ketones, hydrazides, N-hydroxysulfosuccinimides, N-hydroxysuccinimides, maleimides, imidoesters, active halogens, pyridyl-disulfides, isocyanates, nitrobenzoyloxysuccinimides, nitrobenzenes, imidoesters, photo-activatable azidophenyls and azidopolyaromatics, as well as zero-spacer carbodimide catalysts. The preferred polymer is PEG 5,000 with a terminal aldehyde for covalent attachment to surface lysines via Schiff's base formation. We have found that most of the washing and fixation steps for a larger-scale red cell preparation can advantageously be performed in a closed system by utilizing an appliance called the IBM 2991 Cell Washer, which was originally designed for blood banks to facilitate washing of frozen red cell units to remove cryoprotectant agents like DMSO or glycerol just prior to transfusion. The advantage to employing this device for our purposes in preparing freeze-dried red blood cells is that it provides an aseptic environment for the multiple steps of washing and fixation which would otherwise require handling of the red cells in an open container, and the Cell Washer induces less shear stress to resuspend the packed red cells after each step than would be experienced with a resuspension method by hand. As an example, we introduce into the Cell Washer processing bag a volume of 150-200 mL of a suspension of leukodepleted red blood cells at a cell count of $3-4\times10^9$/mL and attach the tubing harness as described in the operating instructions. Then we introduce a volume of 200-250 mL phosphate washing buffer containing 0.1% BSA sterilely through the tubing harness and perform wash cycle #1. At the end of the agitation and spinning period programmed into the 2991, the supernatant washing fluid is automatically expressed out to waste and fresh buffer is introduced thru the harness for a total of three washes. After the spinning step of the third wash, a fixation solution containing 0.05% glutaraldehyde in Hank's buffered salt solution [HBSS] is introduced for a timed incubation of 20 minutes at room temperature before spinning, and then three more washing steps are performed with the phosphate buffer. At this point the fixed, washed red cell suspension is removed from the 2991 processing bag and handled in vials and bottles for the bulking and freeze-drying steps.

3. Compounds to be Delivered.

Examples of compounds that may be coupled to platelets to produce active agents of the present invention include, but are not limited to, nucleic acids such as RNA, DNA, proteins or peptides (enzymes, antibodies, etc,), viruses, bacteria, small organic compounds (e.g., monomers), synthetic and semisynthetic polymers, nanoparticles, chelated metals and ions, etc. Such compounds may have any suitable function or activity depending upon the particular object of the treatment or method, including but not limited to antimicrobial, antibacterial, or antiviral activity; blood coagulation or anti-coagulation activity; reporter or detectable activity, etc. Additional examples of compounds that may be coupled to platelets to produce active agents of the present invention include, but are not limited to, vasoactive, antioxidant, antithrombotic, anticarcinogenic, antiatherogenic, antimitotic, antiangiogenic, and antiproliferative compounds. It will be appreciated that all such compounds can be contained within a vesicle, micelle or other particle which is in turn associated with or coupled to the platelet.

Antiviral compounds. In one embodiment of the present invention, the compound carried by the platelets is an antiviral compound. Any suitable antiviral compound can be used, including but not limited to sialic acid analogues, amantadine, rimantadine, zidovudine, vidarabine, idoxuridine, trifluridine, foscarnet, etc. In one embodiment the antiviral compound is a purine nucleoside analog, examples of which include but are not limited to acyclovir, didanosine, ribavirin, ganciclovir, and vidarabine, and antisense nucleosides, RNA and DNA.

In one embodiment of the invention, platelets carrying antiviral compounds are administered to patients afflicted with a viral infection in an amount sufficient to treat the viral infection. In one embodiment the patient is infected with a hemorrhagic fever viruses, such as a virus of the Filoviridae, Arenaviridae, Bunyaviridae or Flaviviridae families.

Blood coagulation and anticoagulation proteins. The compound to be delivered may be a drug coagulation protein, such as Factor VII, Factor IX, Factor X, Factor XII, Protein C, Protein S, Prothrombin, anticoagulation proteins such as activated protein C, protein S, heparin and heparinoids, and pro- or anti-coagulation proteins of reptile or insect origin, and others.

Such compounds are known. For example, Factor VII or Factor VIIa which may be utilized in carrying out the present invention (this term including modified Factor VII or Factor VIIa or Factor VII analogs which retain the blood coagulation activity of Factor VII) is described in, among others, U.S. Pat. Nos. 6,461,610; 6,132,730 6,329,176; 6,183,743; 6,186,789; 5,997,864; 5,861,374; 5,824,639; 5,817,788; 5,788,965; 5,700,914; 5,344,918; and 5,190,919. In one embodiment, recombinant human Factor VIIa is preferred.

In one embodiment of the invention, platelets carrying blood coagulation proteins are administered to a subject afflicted with a wound in an amount effective to promote blood coagulation at the wound and/or healing of the wound.

Nucleic Acids. Nucleic acids to be carried by platelets of the present invention may encode a detectable protein or peptide such as Lac-Z, beta-glucuronidase, horseradish peroxidase, a fluorescent protein such as green fluorescent protein, etc.

In one embodiment of the invention, platelets carrying nucleic acids encoding a detectable protein are administered to a subject in an amount effective to express the detectable protein in atherosclerotic tissue or plaques in blood vessels to thereby produce an improved animal model of atherosclerosis. Such animals (which preferably are animals that, by diet and/or breeding are susceptible to atherosclerosis) may be administered a putative antiatherogenic compound, and/or antiatherogenic diet, and then compared to a control animal that has not been administered the putative anti-atherogenic compound and/or anti-atherogenic diet, and the extent of atherogenic plaque formation in experimental animals versus control animals compared by visualizing plaques through expression of the detectable protein.

In other embodiments of the invention, the nucleic acid may encode a therapeutic protein or peptide. Examples include, but are not limited to, nucleic acids encoding an anti-atherogenic protein or peptide such as DNA encoding the ras binding domain (RBD) of the ras effector protein $RGL_2$ (e.g., to inhibit proliferation), DNA encoding endothelial nitric oxide sythetase variants (e.g., to inhibit platelet function), DNA encoding the NF-κB super-repressor (e.g., to inhibit inflammatory processes).

4. Associating Compounds with Platelets.

Compounds to be delivered may be associated with platelets by any suitable technique, including but not limited to: (1) directly chemically coupling the compound to be delivered to the platelet surface membrane; (2) conjugating the compound to be delivered to a polymer that is in turn coupled to the platelet's internal membrane; (3) incorporating the compound to be delivered into unilamellar or multilamellar phospholipid vesicles that are in turn internalized into the platelets; (4) absorbing or internalizing the compound to be delivered into nanoparticles, e.g., buckminsterfullerene, that are in turn internalized into the platelets; (5) coupling the compound to be delivered to proteins that are internalized for trafficking to alpha granules in the platelets; (6) coupling the compound to be delivered to proteins (or other macromolecules) or particles that are phagocitized by the platelets; (7) hydrophobically partitioning the compound to be delivered into membranes; (8) physically entrapping the compound to be delivered in the platelet intracellular space through pores that are formed with electrophoration, complement treatment, lytic protein exposure, etc; (9) adsorbing the compound to the exterior surface of the cell by non-covalent physical or chemical adsorption, that are in turn internalized into the platelets.

Cross-linking chemistry for preparing compound-platelet conjugates. Compound-platelet conjugates in which platelets are coupled to proteins, antiviral compounds or the like may be prepared with homo- or hetero-bifunctional cross-linking reagents that can contain, but are not limited to, the following reactive moieties: aldehydes, ketones, hydrazides, N-hydroxysulfosuccinimides, N-hydroxysuccinimides, maleimides, imidoesters, active halogens, pyridyl-disulfides, isocyanates, nitrobenzoyloxysuccinimides, nitrobenzenes, imidoesters, photo-activatable azidophenyls and azidopolyaromatics, as well as zero-spacer carbodimide catalysts. Multi (poly) functional reagents with on or more of these moieties are also considered, as are combinations of two or more cross-linkers, either serially reacted or reacted in concert. The cross-linking step can be carried out in the presence of antioxidants and free-radical scavengers, and the cross-linking reaction can be quenched by adding compounds that contain primary amines. After cross-linking, excess reagent can be removed with methods that include but are not limited to with differential centrifugation, chromatography and/or dialysis.

Viral encapsidation. In the case of nucleic acids to be delivered, the nucleic acid may be encapsidated or enclosed within a viral capsid or particle, which viral capsid or particle may in turn be conjugated or coupled to the platelets. One suitable virus into which the nucleic acid may be encapsidated is the adeno-associated virus (AAV). The AAV virus is known and a nucleic acid of interest to be delivered may be encapsidated or packaged therein in accordance with known techniques. See, e.g., U.S. Pat. Nos. 6,548,286; 6,491,907; 6,489,162; 6,458,587; 6,410,300; 6,268,213; 6,204,059; 6,093,570; 6,057,152; 6,040,183; 5,869,305; 5,863,541; 5,773,289; 5,753,500; 5,478,745; 5,436,146; and 5,139,941. In addition to AAV, it will be appreciated that other viruses, including but not limited to such as adenoviruses, lentiviruses, hepatitis viruses, herpesviruses, can also be used to encapsidate a nucleic acid for association with a platelet to carry out the present invention.

Once the nucleic acid of interest is encapsidated or packaged in a viral particle, viral particles may be associated with or coupled to platelets in accordance with known techniques.

In general, the compound to be delivered is coupled to or associated with the platelets so that each platelet carries, or has associated therewith, at least 1,000, and more preferably at least 10,000, individual molecules of the compound to be delivered.

Once prepared, the platelets with associated compound to be delivered comprise an "active agent" which may be stored in frozen form, refrigerated, or at room temperature (depending upon the shelf life required) for subsequent reconstitution and use.

5. Reconstitution and Administration of Active Agents.

Pharmaceutical formulations of the present invention may simply comprise dried (preferably lyophilized) blood cells carrying the active agent, pyrogen-free and sterile in a sterile aseptic package. Albumin may be included, as noted above. Pharmaceutical formulations may also comprise a platelet preparation of the present invention reconstituted in a pharmaceutically acceptable carrier. Additional agents, such as buffers, preservatives, and other therapeutically active agents, may also be included in the reconstituted formulation. See, e.g., U.S. Pat. No. 4,994,367 (the disclosure of which is incorporated herein by reference). The amount of blood cells and pharmaceutical carrier is not critical and will depend upon the particular application of the blood cells, whether or not they have been rehydrated, etc., but in general will range from 1 or 10 percent by weight blood cells up to 90 or 99 or even 99.9 percent by weight blood cells, and from 0.01, 1 or 10 percent by weight of pharmaceutically acceptable carrier up to 90 or even 99 percent by weigh pharmaceutically acceptable carrier. In some embodiments of fixed-dried blood cells that have not been rehydrated the composition may consist essentially of or consist entirely of the fixed-dried blood cells, free of any particular carrier.

The fixed-dried blood cells described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the fixed-dried blood cells may be admixed with, inter alia, an acceptable carrier. The carrier must, of course, be acceptable in the sense of being compatible with any other ingredients in the formulation and must not be deleterious to the patient. The carrier may be a solid (including powders), and is preferably formulated with the blood cells and packaged as a unit-dose formulation, for example, a bottle of lyophilized powder which may be reconstituted by addition of an aqueous solution.

For rehydrating the blood cells, any aqueous carrier which rehydrates the platelets so that they possess the characteristics enumerated above and are suitable for intravenous injection may be used (e.g., sterile, pyrogen free, physiological saline solution). For example, an aqueous carrier may be injected into a bottle containing a pharmaceutical formulation of the invention in the form of a lyophilized powder, the contents agitated if necessary, and then the pharmaceutical formulation in the form of an aqueous suspension of rehydrated fixed-dried blood cells withdrawn from the bottle and administered by injection into a patient.

The compounds of the invention are preferably administered internally, e.g., orally or intravenously, in the form of conventional pharmaceutical compositions, for example in conventional enteral or parenteral pharmaceutically acceptable excipients containing organic and/or inorganic inert carriers, such as water, gelatin, lactose, starch, magnesium stearate, talc, plant oils, gums, alcohol, Vaseline, or the like. The pharmaceutical compositions can be in conventional solid forms, for example, tablets, dragees, suppositories, capsules, or the like, or conventional liquid forms, such as suspensions, emulsions, or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical compositions may also contain other therapeutically active materials. The pharmaceutical compositions of the invention can be made using conventional methods know in the art of pharmaceutical manufacturing.

Reconstituted pharmaceutical formulations of the present invention are typically administered to human patients by parenteral administration (e.g., intravenous injection, intraarterial injection). The amount of the pharmaceutical formulation administered will vary depending upon the weight and condition of the patient, but will typically range from 20 to 350 milliliters in volume, and from $1 \times 10^9$ to $3 \times 10^9$ platelets per milliliter (and more preferably from $2 \times 10^9$ to $3 \times 10^9$ platelets per milliliter) in concentration. Pharmaceutical formulations may be packaged in a sterile, pyrogen free container to provide these volumes and dosages as a unit dose. The particular route of administration is not critical and will depend upon the condition being treated, with topical administration or application into penetrating wound sites also being utilized for such injuries and their corresponding treatments.

Three applications, involving wound site imaging, coagulation factor delivery and antiviral delivery, are among those considered in the following discussion.

a) RL Platelets for Wound Localization with Magnetic Resonance Imaging—

RL platelets can be loaded with paramagnetic nanoparticles that can function as MRI contrast agents when the rehydrated cells localize to the sites of vascular injury. Two recent advances have provided the tools to prepare RL platelet-MRI contrast agent formulations. First, infusible gadolinium (Gd)-chelates have been approved by the FDA (e.g., Magnevist™) and are proving useful, as a relaxation contrast agent, for the evaluation of vascular pathologies (e.g., Rofsky and Adelman, 2000). A wide range chemically activated of Gd-chelators for attachment to primary amines on macromolecules are available, and have lead to the development of research probes for specific angiographic imaging applications (see Artemov, 2003, for a review). For example, fibrin clots have been localized with Gd-anti-fibrin antibody probes for the detection of vulnerable plaques (Flacke et al., 2001).

Secondly, major advances have been made in the preparation of magnetic nanoparticles (see Pankhurst et al, 2003, for a review). Of particular importance is the synthesis of iron oxide (maghemite and magnetite) nanoparticles with narrow size distribution (Chatterjee et al, 2003). Furthermore, methods for the modification of iron oxide particles with polymers for the attachment of macromolecules have been developed (Chatterjee et al. 2003) and used to isolate blood cells in magnetic fields (Chen, et al., 2000). The RL platelet represents a unique platform for targeting iron oxide nanoprobe fabrication and Gd-chelates to sites of vascular injury.

b) RL Platelet-coagulation Factor Conjugates for Hemostasis in Coagulopathic Conditions—

The tethering of coagulation factors (such as FVIIa) to the surface of RL platelets and/or loading of α-granules etc) with coagulation factors (FXIIIa for clot stabilization, caged thrombin for photoactivation (Arroyo et al., 1997)), is a logical strategy for delivering replacement factors to vascular wound sites in hemophiliacs that have circulating antibody inhibitors to standard replacement therapeutics (refractory hemophiliacs) as well as patients with other types of coagulopathies. Recombinant FVIIa has been hypothesized to provide hemostasis through two mechanisms that are operant on the platelet surface. First, the ability of recombinant factor VIIa (rFVIIa) to provide hemostasis in hemophilia patients (Hedner and Glazer, 1992) has been theorized to involve the direct activation of factor Xa on the surface of platelets (e.g., see Monroe et al., 1997 and 2000), thus "bypassing" the need for factors IX and VIII. This "bypass" activity of the rec FVIIa might be the functional basis for the utility of the Novo Nordisk product as a hemostatic agent in hemophilia A and B. Secondly, in the presence of normal levels of coagulation factors, rFVIIa might augment hemostatic mechanisms by activating factor IX on the platelet surface. Thus, rFVIIa mediation of thrombin generation on the platelet surface might compensate for a lack of platelets in thrombocytopenia or a lack of proper platelet function in thrombasthenia. The hypothesis that rFVIIa can play a "compensating" role for platelet function(s) is supported by the clinical observation that rFVIIa can improve hemostasis in patients that are thrombocytopenic (e.g., Poon et al., 2000, Kristensen et al., 1996), thrombasthenic (e.g., Al Douri et al., 2000) or are those affected by both platelet defects, such as in trauma (e.g., Dutton et al., 2003). However, high-doses of rFVIIa are frequently required for hemostasis, perhaps due to the low (Kd ~90 nM) affinity of the coagulation factor for the platelet surface (Monroe et al., 1997). We thus hypothesize that the direct chemical tethering of rFVIIa to the platelet surface will improve the therapeutic effectiveness (index) of the recombinant protein as a hemostatic agent to stop active bleeding c) Antiviral Delivery with Lyophilized Platelets—

RL platelets and RL RBCs hold promise for delivering antiviral therapeutics to macrophages that are infected with the single strand RNA viruses that cause hemorrhagic fevers and hepatitis. This is important because the macrophages of the reticuloendothelial system (RES) are involved in the initial stage of viral infection, as well as macrophages at sites of vascular injury in the later acute-hemorrhagic phase of infection. Viruses of the Arenaviridea (e.g., Lassa fever virus), Filoviridae (e.g., Ebola and Marburg viruses), Bunyaviridae (e.g., Rift Valley virus) and Flaviviridae (e.g., Yellow fever virus) families cause viral-induced cellular damage to vascular tissues that result in hemorrhage. Similarly, hepatitis C virus (a Flaviviridae family member) propagation is frequently associated with bleeding-intensive hepatic surgeries. Ribavirin, as a broad-spectrum antiviral RNA mutagen, holds promise for the treatment of these hemorrhage-associated viruses. However, adverse toxicities have limited the clinical use of this ribonucleoside as an antiviral chemotherapeutic. We seek to increase the therapeutic efficacy of ribavirin by using RL platelets to deliver the ribonucleoside. The intrinsic hemostatic function of RL platelets will thus concentrate the ribavirin in the microenvironment of the virus for increased chemotherapeutic efficacy; in RES and vascular wound site macrophages.

The present invention is described in greater detail in the following non-limiting Examples.

EXAMPLES 1-5

Attachment of Ribavirin to Platelets

These examples describe methods for the preparation and characterization of reconstituted platelets having ribavirin and rFVIIa coupled thereto.

Example 1

Synthesis of Ribavirin-Polylysine Polymers

Ribavirin is chemically phosphorylated for ribavirin monophosphate (RMP) as detailed by Yoshikawa et al., *Tetrahedron Lett.* 50, 5065-5068 (1967)). Ribavirin monophosphate (RMP) is coupled to polylysine via a pH-sensitive phosphoramide linkage in accordance with the procedure of Di Stefano and Fiume (*Trends in Glycosci. and Glycotech.* 50, 461-472 (1997)) or a simplified procedure is based on the formation of an imidazole-ribavirin adduct (see Chu et al., *Nuc. Acids. Res.* 11, 6513-6529 (1983)). The conjugation chemistry for ribonucleosides polymer synthesis was tested with uracil rather than ribavirin. We do not anticipate that the difference in nitrogenous base structure between uracil and ribavirin will have a large effect on the synthesis.

Polylysine (<mw>=205 kDa for ~1,400 residues lysine/molecule) was reacted with FITC (fluorescein isothiocyanate) and SANPAH (N-succinimidyl-6-[4'-azido-2'-nitrophenylamino]hexanoate) to respectively provide a fluorescent label and a photoactivatable moiety for the covalent attachment of the final product to the platelets. Uracil was coupled to the lysine side-arms by first activating UMP with imidazole with EDAC (1-ethyl-3-(3-dimethylaminopropyl) carbodiimide) as a catalysis. The activated UMP~imidazole complex was then added to the FITC/SANPAH-modified lysine chain to form phosphoamide bonds. Based on peak sizes from proton NMR analysis (α-carbon proton vs. nitrogenous base protons, see FIG. 1, "Proton NMR Spectra of Nucleoside Copolymer" 12% of the lysine residues were coupled to UMP. The final average composition of the 1400 residue copolymer was 168, 20 and 4 lysine side-arms modified respectively with uracil, SANPAH and FITC, leaving ~1200 lysine residues unmodified.

In a separate series of reactions, epsilon amino groups of polylysine (Sigma-Aldrich, <MW>=200,000 kDa) are modified with FITC to provide a fluorophoric label and with the heterobifunctional cross-linker SANPAH (Pierce) to provide a moiety for the photochemical attachment to platelets in the next step (b). FITC and SANPAH are attached to the polylysine for one FITC moiety/~300 lysine residues and one SANPAH moiety/~30 lysine residues. RMP is imidazolated and then coupled to the FITC, SANPAH polylysine to form the phosphoramide bond for the ribavirin copolymer as detailed by Chu et. al. (supra). The goal is to saturate the lysine residues with RMP residues. Proton and $^{13}C$ NMR are performed to characterize the extent of polymer modification.

The pH sensitivity of the phosphoamide bond (see Fume et al., *Pharm. Acta. Helv.* 137-139 (1988)) is verified by incubating the ribavirin copolymer in buffers with pHs varying between 2.4 and 7.4 for one hr. After the incubation, pHs are adjusted to neutrality and dialyzed vs. PBS to remove free RMP. The samples ds examined with proton NMR to determine the extent of hydrolysis. The rate of hydrolysis should increase as the pH is lowered from neutrality.

We choose to test the conjugation chemistry for ribonucleosides polymer synthesis with uracil rather than ribavirin because of the temporary unavailability of the antiviral immediately before and during the military operation in Iraq. We do not anticipate that the difference in nitrogenous base structure between uracil and ribavirin will have a large effect on the synthesis.

Example 2

Figure 2:
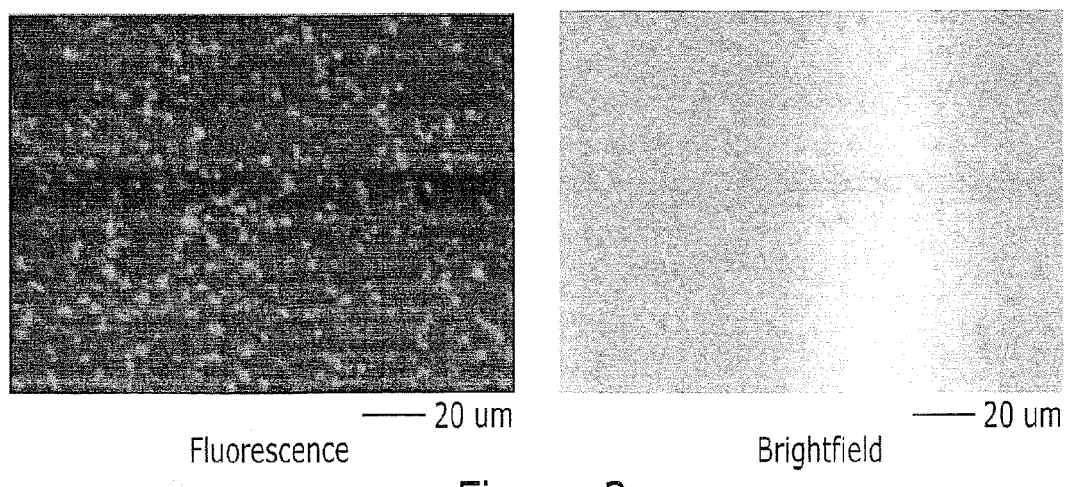
FIG. 2 shows the fluorescent microscopy of polymer-modified RL platelets.

Attachment of Ribavirin-Polylysine Polymers for Ribavirin-Loaded Lyophilized Platelets The procedure for preparing lyophilized platelets involves four steps: Removal of platelets from excess plasma proteins, mild paraformaldehyde cross-linking to stabilize cellular structures, removal of platelets from unreacted cross-linker and lyophilization (Read et al, U.S. Pat. No. 5,651,966). After removal of the excess paraformaldehyde, the platelets are mixed with varying concentrations of the ribavirin polymer and exposed to visible light to activate the SANPAH moieties for the formation of covalent linkage with the platelet surface. The platelets are then lyophilized with standard procedures. Platelets are prepared with different amounts of ribavirin by varying the concentration of ribavirin-copolymer in the coupling step. The ability of the ribonucleoside copolymer to covalently couple to RL platelets was studied by incubating the cells with the delivery polymer in visible-spectrum light to photoactivate the SANPAH moiety for covalent coupling. Unreacted copolymer was removed with centrifugational washing, and then the platelets were examined with fluorescent microscopy. FIG. 2, "Fluorescent Microscopy of Polymer-Modified RL Platelets", demonstrates that he fluorescent-labeled ribonucleoside copolymer associated with the cells. Based on the average fluorescent intensity of the platelets, each cell was covalently labeled with 24,800 copolymers.

Example 3

Characterization of Ribavirin-Platelets

Ribavirin-platelets prepared in accordance with example 2 above are rehydrated with normal saline and then subject to analysis to verify chemical nature of the copolymer attachment, the functionality of the platelets and the ability of the ribavirin-platelets to release the ribonucleoside.

Surface density and cellular distribution of the ribavirin-polylysine polymer. Ribavirin-loaded platelets are subjected to liquid scintillation counting, and then the amount of attached [$^3H$]ribavirin-copolymer per platelet calculated from the specific activity of the radiolabel. Flow cytometry may also be performed to assess the relationship between fluorescence intensity and the number of copolymers per platelet. The cellular localization of the [$^3H$]ribavirin-copolymer may be ascertained with confocal microscopy from the fluorescence of the FITC moiety.

The chemical integrity of the ribavirin units is verified by placing the ribavirin-platelets in low pH buffer to hydrolyze the nucleoside. Samples will then be subjected to TLC analysis (as detailed in Fischer et al, *Brit. J. Haem.* 111, 167-175 (2000)) to determine if the [$^3H$hydrolysis product co-elutes with [$^3H$]ribavirin monophosphate standards.

The activation response of ribavirin-platelets. Platelets loaded with increasing amounts of [$^3H$]ribavirin-copolymer are subjected to the same type of analysis that was utilized to characterize reconstituted lyophilized platelets prepared for transfusion purposes. Briefly, the morphology of activated and unactivated ribavirin-platelets is examined with scanning and transmission electron microscopy. vWf-mediated adhesion may be investigated with ristocetin aggregation. The surface density of phosphatidylserine, p-selectin, activated GPIIb/IIIa and fibrinogen may be ascertained with flow cytometry. These procedures may be used to confirm the maximum degree of copolymer modification that can be obtained without unduly adversely affecting hemostatic function and hence optimize any particular preparation protocol.

Endocytosis of ribavirin platelets by macrophages for drug release and antiviral activity. This analysis utilizes a tissue culture-based splenic macrophage phagocytosis system that has been detailed elsewhere (Fischer et al., *Art. Cell. Blood Subs. Imm. Biotech.* 29, 439-451 (2001)). The antiviral activity of ribavirin-RL platelets may be assessed by infecting the rat splenic macrophages with the Adames strain of Punta Toro virus, since it can be handled under level 2 biosafety conditions, is known to infect rodent macrophages, causes a lethal hepatic necrosis in infected mice, and is sensitive to the antiviral effects of ribavirin in vivo and in vitro. Alternatively these studies can optionally be adapted to mouse macrophage cultures, which are known to be highly permissive for Punta Toro virus replication.

The [$^3$H]ribavirin-copolymer-RL platelets are incubated with the macrophages with gentle rocking at 37° C. Samples are withdrawn as a function of time and subjected to two types of analysis to respectively follow a) platelet internalization for viral inactivation and b) ribavirin metabolism.

Platelet phagocytosis and viral inactivation. These studies employ fluorescent microscopic and flow cytometric analysis to identify macrophages (PE fluorescence from anti-macrophage-PE) and ribavirin-RL platelet phagocytosis (from [$^3$H]ribavirin-copolymer FITC fluorescence). The cell mixtures are incubated with anti-macrophage-PE conjugate (MCA-342, Serotec) to label the macrophages, then flow cytometry and confocal fluorescence microscopy are performed to follow the internalization and phagocytic processes. Flow cytometry may be relied upon to provide quantitative data, while confocal microscopy may be performed to examine the distribution of the ribavirin-platelets that are docked to and/or internalized by macrophages.

A subset of macrophages treated with ribavirin-RL platelets or control platelets may be infected in triplicate with Punta Toro virus at a multiplicity of infection of 10 for one hour at 37° C. At this point, the cells are washed 3 times with room temperature growth medium, and maintained in growth medium at 37 degrees C. After completing the washes, a sample of growth medium is removed from each well for analysis of viral levels by plaque assay. Additional samples are removed at four-hour intervals to determine levels of virus within the supernatant. Viral titers will be assessed by plaque assays on Vero cells, which are permissive for Punta Toro virus infection and have been used previously to titer Punta Toro virus levels by plaque assay. Alternatively, cells are infected with Punta Toro virus prior to treatment with ribavirin-RL or control platelets. This will assess whether ribavirin-RL platelets can control previously established infections. As a positive control for these studies, groups of macrophages are infected with Punta Toro virus in triplicate. These cultures are then treated with ribavirin (not loaded on platelets) at a concentration ranging from 4-10 micrograms per ml, a concentration range that has previously been shown to inhibit Punta Toro virus replication in vitro. Ribavirin-RL platelets are considered to exhibit antiviral effect if they decrease viral titers in treated macrophage cultured to levels that are comparable to those observed with conventional ribavirin treatment.

Ribavirin metabolism. The time course of [$^3$H]ribavirin-monophosphate release and metabolism is examined by lysing cell mixtures with TX-100 and then resolving free nucleosides with TLC analysis (Fischer et al., 2000, supra). This information is used to verify the release of [$^3$H]ribavirin monophosphate from the copolymer as well as the conversion to [$^3$H]ribavirin-diphosphate and triphosphate.

Example 4

Characteristics of Platelets

Preferably platelets with at least 100,000 ribavirin copolymers per cell that function with 90% efficiency in the ristocetin aggregation analysis are obtained by the procedures described above (or modifications thereof which will be readily apparent to those skilled in the art). These criteria are chosen for two reasons. First, a 10% reduction in the ristocetin in vitro hemostasis parameter has an insignificant effect on in vivo hemostatic function of RL platelets as judged by the ability to correct bleeding in thrombocytopenic rabbits. Second, the delivery of 100,000 ribavirin-copolymer molecules on a single platelet represents $\sim 3\times 10^8$ ribavirin moieties (or $\sim 5\times 10^{-16}$ moles of ribavirin). If a single macrophage (with an intracellular volume of $\sim 10^3$ um$^3$) internalizes a single ribavirin-platelet, the intracellular concentration of ribavirin functions will be $\sim 5\times 10^{-19}$ moles/um$^3$ or $\sim 5\times 10^{-4}$ moles/liter (500 uM). This is a concentration that is well above the range of ribavirin (10-100 uM) that exhibits antiviral activity in tissue culture (see e.g. Crotty et al., J. Mol. Med. 80, 86-95 (2002)).

Figure 3:
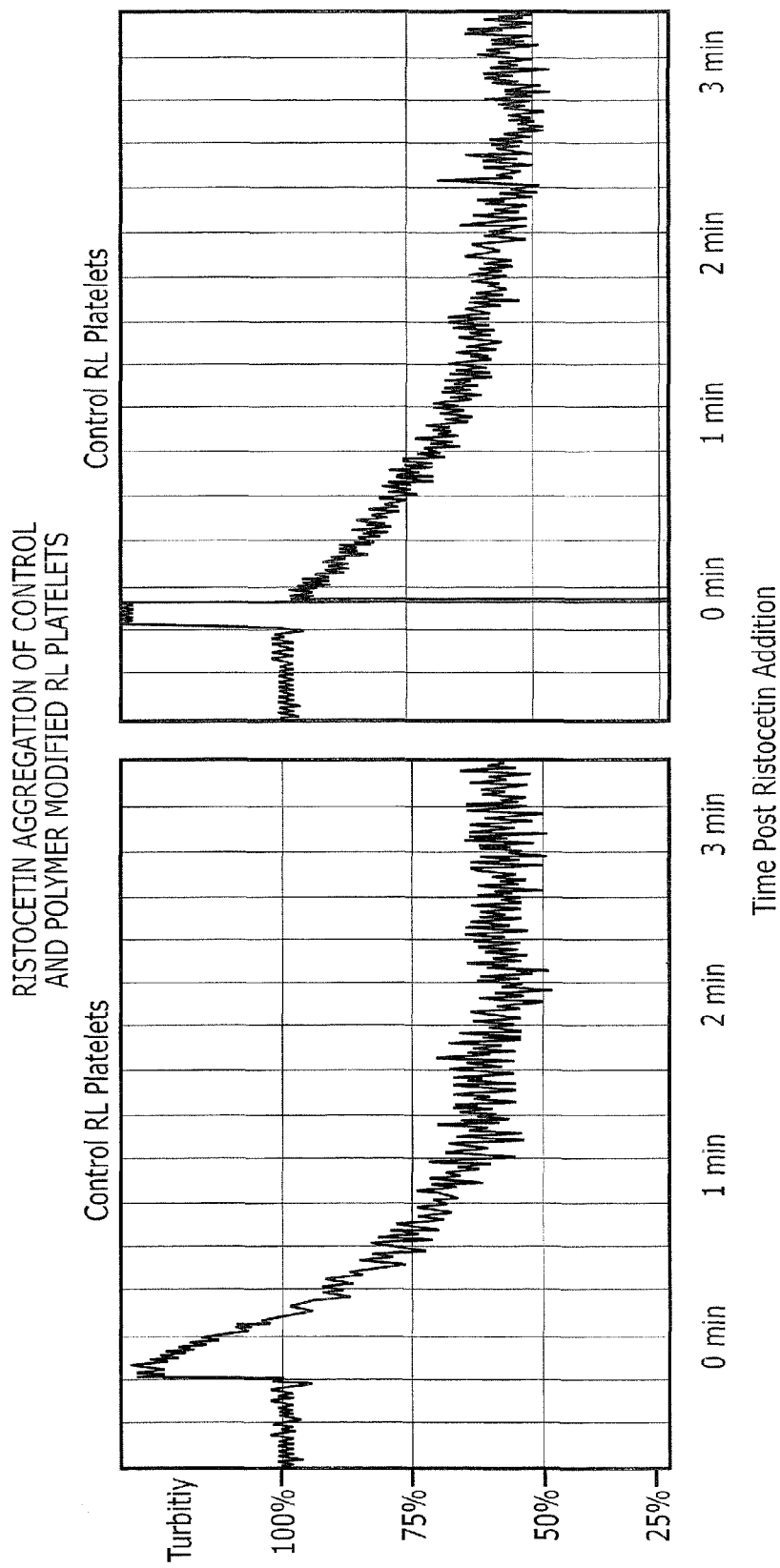
FIG. 3 shows ristocetin aggregation of control and polymer modified RL platelets.

The in vitro metrics that are most correlative with in vivo hemostatic efficacy for RL platelets are related to GPIb-von Willebrand factor mediated adhesion. We thus utilized ristocetin-mediated aggregation for the preliminary functional characterization of the ribonucleoside-labeled RL platelets. FIG. 3, "Ristocetin Aggregation of Control and Polymer Modified RL Platelets" demonstrates that after rehydration, the labeled cells retained ~70% of functionality as judged by the initial slope and extent of aggregation curves.

Example 5

Internalization of Ribavirin in Platelets

In an alternative embodiment of the foregoing, the ribavirin is modified for platelet internalization. For example, this is carried out by coupling the short chain ribavirin polylysine copolymers to IgG or fibrinogen for alpha granule uptake. Alternatively, latex nanoparticles are loaded with ribavirin for platelet endocytosis, and then cells will processed for lyophilization.

EXAMPLES 6-8

Lyophilized Platelets for Delivery of Nucleic Acids

These examples describe methods for using rehydratable, lyophilized (RL) platelets to deliver nucleic acids to sites of vascular injury for drug development, diagnostic, or therapeutic purposes. The nucleic acid may encode any protein or peptide of interest, such as a reporter protein or peptide for use in diagnostic or drug screening purposes.

Figure 4:
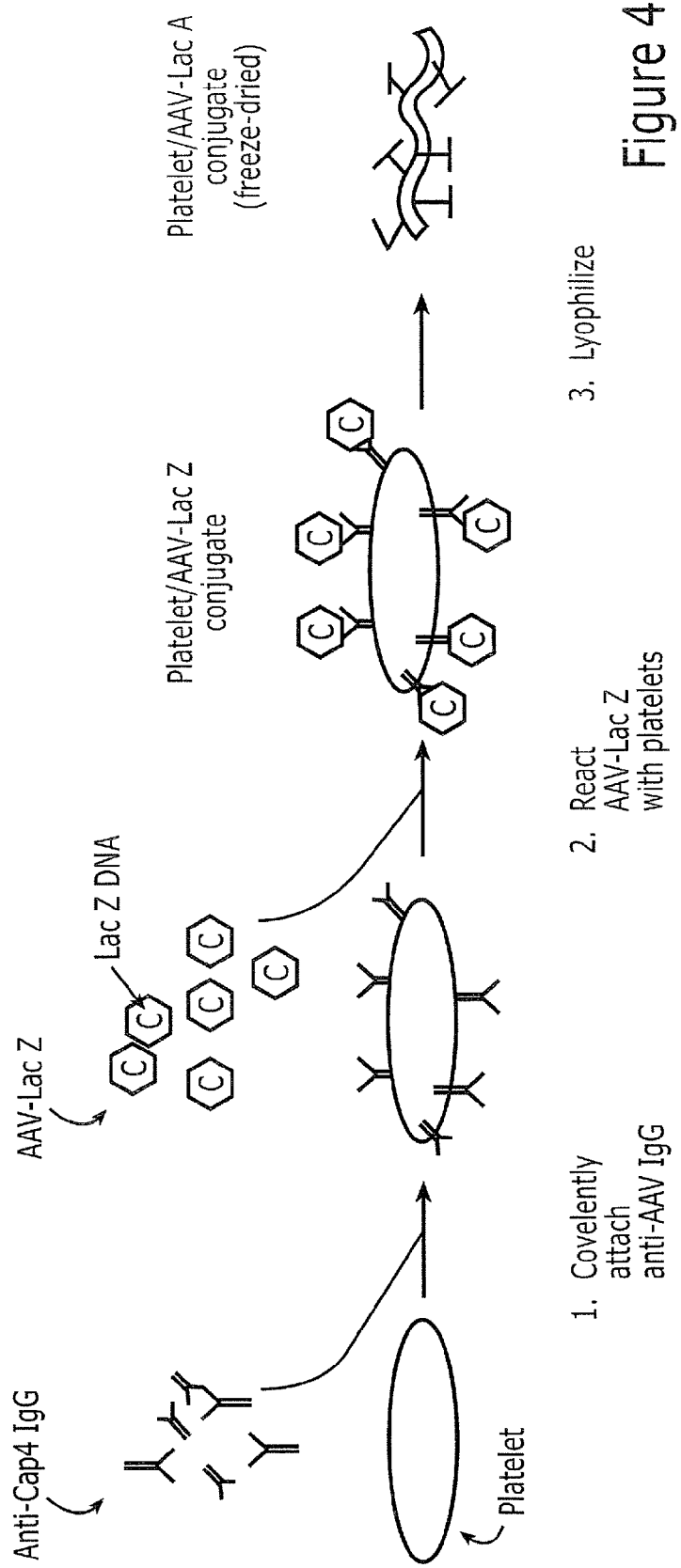
FIG. 4 schematically illustrates the preparation of Platelet/AAV~Lac Z reporter conjugates.

RL platelet/AAV~Lac Z conjugates are prepared as depicted in FIG. 4, "Preparation of Platelet/AAV~Lac Z Reporter Conjugates" herein. The procedure is a variation of the procedure described in Read et al., U.S. Pat. No. 5,651, 966.

Example 6

Attachment of Anti-AAV Antibodies to Platelets

Preparation of Platelets for Antibody Attachment. Fresh Porcine Platelets are isolated with differential centrifugation (to obtain platelet-rich plasma) and Sepharose CL2B chromatography (to free platelets from plasma proteins) in accordance with known techniques (Read et al., 1Proc. Natl. Acad. Sci. USA 92, 397-401 (1995)). The cells are then be stabilized with paraformaldehyde and washed with centrifugation to remove unreacted cross-linker. These steps will employ known protocols that have been detailed elsewhere (Read et al., supra).

Modification and attachment of anti-AAV antibody to platelets. Anti-AAV capsid protein VP1 polyclonal antibody (Research Diagnostics Inc, Pleasant Hill, N.J., ALS24107) polyclonal antibody (to residues 278-289 on the capsid protein) is reacted with N-succinimidyl 3-[2-pyridylthio]propionate (SPDP) to form lysine-imide linkages between the cross-linker and the antibody in accordance with known techniques (see Carlsson et al., *Biochemistry J.* 173, 723-737 (1978)). Excess cross-linker is removed with sizing chromatography, and then the thiol-activated antibody is incubated for 2 hr with the aldehyde stabilized platelets prepared as above for attachment of the antibody to the platelet surface via sulfhydryl moieties. The reaction stoichiometry is 10,000 anti-capsid antibodies per platelet. Unbound antibody is removed with two centrifugation washes.

Attachment of AAV~Lac Z to platelets for lyophilized platelet/AAV~Lac Z conjugates. AAV~Lac Z is prepared with "triple-plasmid" transfection methods in which 293 cells are co-transfected with three plasmids: pAAV with Lac Z, a second plasmid with Rep and Cap genes, and a third plasmid that encodes adenovirus proteins that mediate the "rescue" step (see Monahan and Samulski, *J. Virol.* 61, 3096-3950 (2000)). With this strategy, the 293 cells do not have to be infected with adenovirus to "rescue" the recombinant AAV particles, thus avoiding adenoviral contamination of the final AAV preparation. AAV~Lac Z is isolated from the 293 cell tissue culture with ammonium sulfate precipitation and density gradient purification in accordance with known techniques.

To attach the AAV~Lac Z to the platelet surface, the platelets are incubated for three hours with the platelet~anti-capsid IgG conjugates prepared as above. Excess AAV~Lac Z is removed with two centrifugation washes. The platelet/AAV~Lac Z conjugates are then frozen, lyophilized and stored at $-20°$ C. The freeze-dried platelet/AAV~Lac Z conjugates are prepared so that upon rehydration, the platelet and AAV~Lac Z concentrations will respectively be $1 \times 10^8$ platelets/ml and $1 \times 10^{12}$ AAV~Lac Z vectors/ml.

Example 7

Characterization of Platelet/AAV~Lac Z Conjugates

Surface density of AAV~Lac Z on the platelets. The amount of anti-capsid protein antibody and AAV~Lac Z that is attached to the platelet surface is quantified by subjecting samples to SDS-PAG electrophoresis and Western analysis. Anti-rabbit IgG is used to detect the anti-AAV, while anti-Capsid VP1 is used to probe for AAV proteins. The object is to attach approximately 100,000 AAV~Lac Z vectors to each platelet. If a lower stoichiometry is obtained by any particular procedure the concentration of the antibody can be adjusted upwards, and/or the incubation time for the platelet reaction with AAV~Lac Z may be increased.

The effect of Lac Z attachment on platelet function. The effect of platelet surface modification with AAV~Lac Z on RL platelet function may be ascertained by performing aggregation assays and Baumgardner analysis in accordance with known techniques (Khandelwal et al., *FASEB J.* 11, 1812 (1997); Bode et al. *J. Lab. Clin. Med.* 133, 200-211 (1999)).

The effect of AAV~Lac Z attachment on transduction efficiency. The effect of surface attachment on AAV~Lac Z transduction efficiency is estimated by incubating the AAV~Lac Z conjugates with porcine splenic macrophages and then probing for gene transfer by staining with X-gal. Control experiments may be performed with titers of AAV~Lac Z that are equivalent to the number of virus particles delivered with the platelets.

An important issue in the development of AAV as a gene therapy tool is difficulties in obtain high titer preparations (e.g., see Monahan and Samulski, supra). By immuno-absorbing AAV~Lac Z to the surface of the platelet, a very high local concentrations of the probe will be produced.

The coupling of AAV to platelets may affect the function of both the viral and platelet systems. If the performance of the platelets in Baumgardner and aggregation assays is measurably affected by the probe attachment, the surface density of the AAV~Lac Z may be reduced. If platelet-bound AAV is found to transduce splenic macrophages with a dramatically reduced efficiency, the surface density of the viral vector may be increased. Alternatively, other viral tethering strategies may be utilized.

Example 8

Reporter Gene Delivery to Sites of Vascular Injury

The ability of RL platelet/AAV~Lac Z conjugates to transduce the Lac Z gene into sites of vascular injury will be investigated. In this example atherosclerotic vessels in pigs on an atherogenic diet are injured, RL platelet/AAV~Lac Z conjugates are infused, and the animals continued on an atherogenic diet to produce additional plaque development at the sites of injury. This design models the sequence of events that occur when a vessel is reoccluded with atherosclerotic plaque after the endothelium is perturbed by atherosclerotic plaque rupture and/or angioplasty. A detailed description of the experiment follows. This system is useful in testing drugs such as statins or the like, or dietary intervention, for activity in treating or relieving atherosclerosis in a subject.

Induction of atherosclerosis. Four $Lpb^{1/1}$ genotype 30-40 kg (young adult) male pigs are used. The $Lpb^{1/1}$ (Lpg=L (lipoprotein), b (apoB100), p (pig)) is a polymorph genotype that has been bred in a closed colony at the Francis Owen Blood Research Laboratory at UNC-Chapel Hill. Inherited in an autosomal co-dominant fashion, the $Lpb^{1/1}$ animals develop a stable degree of hypercholesterolemia on an atherogenic diet and consistently develop moderately severe atherosclerosis that correlates closely with dietary cholesterol levels (Nichols et al., *Am. J. Pathyol.* 140, 403-415 (1992)). Two pigs are placed on a high cholesterol diet and two remain on a standard low-cholesterol feed.

Vascular injury and treatment with RL platelet/Lac Z constructs. After two months on the control or atherogenic diet, the animals are anesthetized and portions of the right femoral artery surgically isolated. Sites of vascular injury are formed by crushing the artery with a Goldblatt clamp at two cm intervals. Five wounds are established over a 10 cm length of vessel. Immediately after establishing the wounds, $10^9$ AAV~Lac Z modified platelets are rehydrated in 10 ml sterile saline and infused into the peripheral ear vein. The surgical incisions are repaired, and then the animals maintained on control or high-cholesterol diets for two additional months.

Post-mortem analysis of tissues. After the post-surgery two months on the control or high-cholesterol diet, the animals are euthanized. The injured portion of the femoral artery, as well as similar portions of the contralateral vessel, are histochemically examined with X-gal staining to probe for the expression of the Lac Z gene product galactosidase. Spleen, lung, cardiac and liver tissue may also be analyzed for expression of the transgene.

Example 9

Coagulation Protein Conjugation and Delivery to a Vascular Wound Site

The preparation of a coagulation protein-platelet conjugate can utilize a heterobifunctional cross-linker such as SANPAH (N-succinimidyl 6-[4"-axido-2'-nitrophenylamino]hexanoate) with a primary amine reactive and photoactivatable moieties for covalent attachment. Various coagulation proteins can be used, including recFVIIa (Novo Nordisk product), FVII or FVIIa and related mutants from various expression systems, as well as coagulation proteins that generate FVIIa, such as FXIIa or FXa. To prepare a RL platelet-red-FVIIa conjugate, a stock solution of 100 mM SANPAH is prepared in anhydrous DMSO, then diluted 1/100 into 1 mg/ml recFVIIa (e.g., from Novo Nordisk) in phosphate buffered saline (10 mM phosphate, 150 mM NaCl, pH=7.4) and allowed to incubate in the dark for 1 hr. Unreacted SANPAH is removed by dialyzing the mixture overnight vs. PBS or gel filtration on Sepharose CL4B.

Platelets are subjected to aldehyde stabilization and then freed from excess paraformaldehyde as detailed in U.S. Pat. No. 5,651,966, and then the SANPAH-recFVIIa is conjugated to the cells. The SANPAH-recFVIIa and the fixed platelets are then mixed for 100,000 platelets/ul and 0.1 mg/ml SANPAH-protein conjugate in PBS, and then exposed to visible range light from a standard fluorescent source for 1 hour to achieve photocoupling of the SANPAH-recFVIIa conjugate to the platelet surface. Unreacted protein is then separated from the platelets with chromatography on Sepharose CL-2B, and then the recFVIIa-platelet conjugates are lyophilized as detailed in U.S. Pat. No. 5,651,966.

Example 10

Coupling of Recombinant Factor VIIa To Surface of Lyophilized Platelets Through Native Binding Sites Preparation of fluorescein isothiocyanate (FITC) labeled recombinant factor VIIa (rFVIIa)-4.8 mg rFVIIa (Novallordisk, infusion grade) rehydrated with 4.8 ml dist. $H_2O$ for [rFVIIa]=20 uM. rFVIIa was dialyzed overnight vs phosphate buffered saline (PBS), then incubated for 30 min at r.t. with 40 uM FITC. The reaction mixture was dialyzed overnight vs PBS, then overnight again vs. citrated saline to obtain rFVIIa-FITC.

Figure 5:
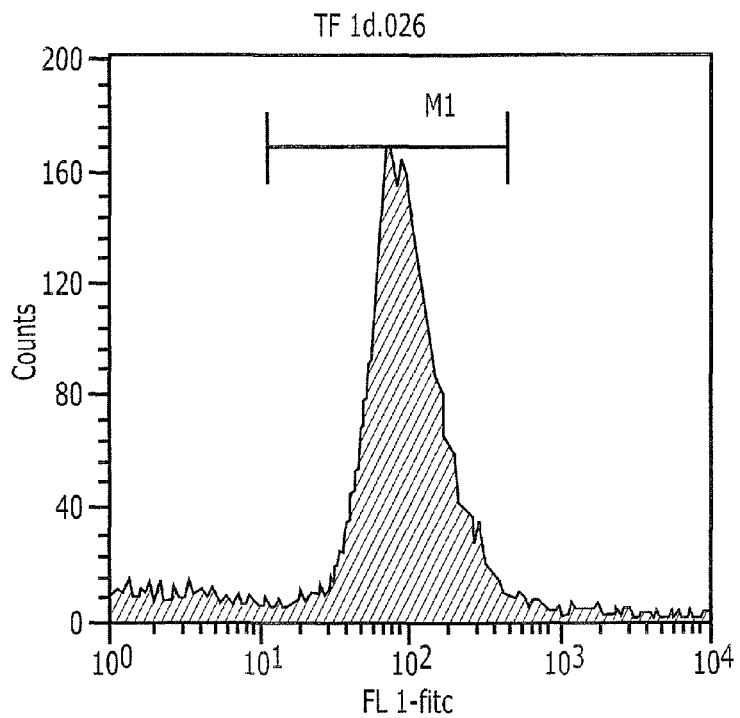
FIG. 5 shows flow cytometric analysis of rFVIIa-FITC bound to RL platelets.
Figure 5:
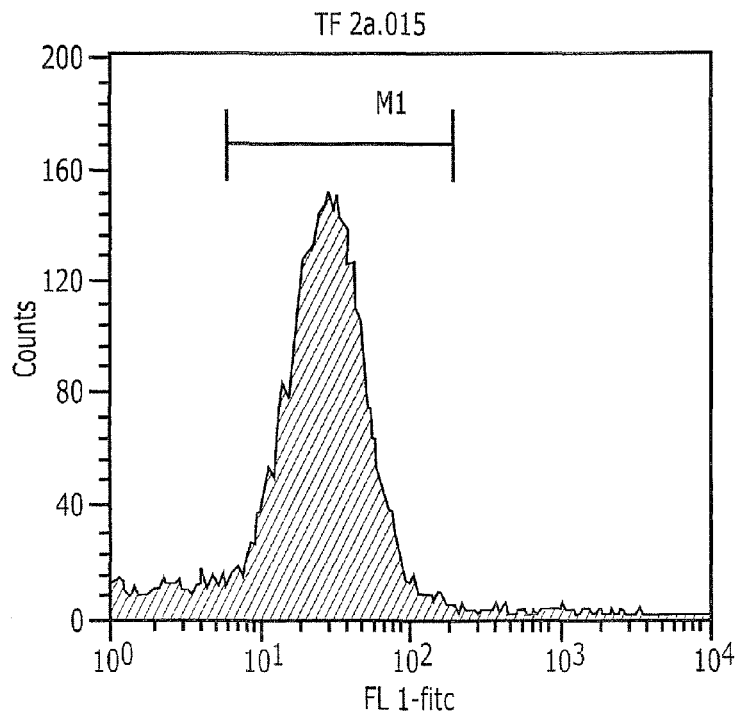

Surface attachment of rFVIIa-FITC to rehydrated, lyophilized platelets-Lyophilized platelets were hydrated with distilled water for $1.89 \times 10^9$ cells/ml. Platelets and rFVIIa-FITC were mixed and incubated at room temperature for 30 minutes at varying concentrations ranging from 0 to 10 uM rFVIIa-FITC and 0 to $1.89 \times 10^9$ cells/ml. The platelets were centrifugally washed once with saline, then diluted into PBS+2% paraformaldehyde for flow cytometric analysis.

rFVIIa-FITC bound to lyophilized platelets in a homogeneous manner based on the symmetrical flow-cytometric histogram (see FIG. 5, "Flow cytometric analysis of rFVIIa-FITC bound to RL platelets).

Figure 6:
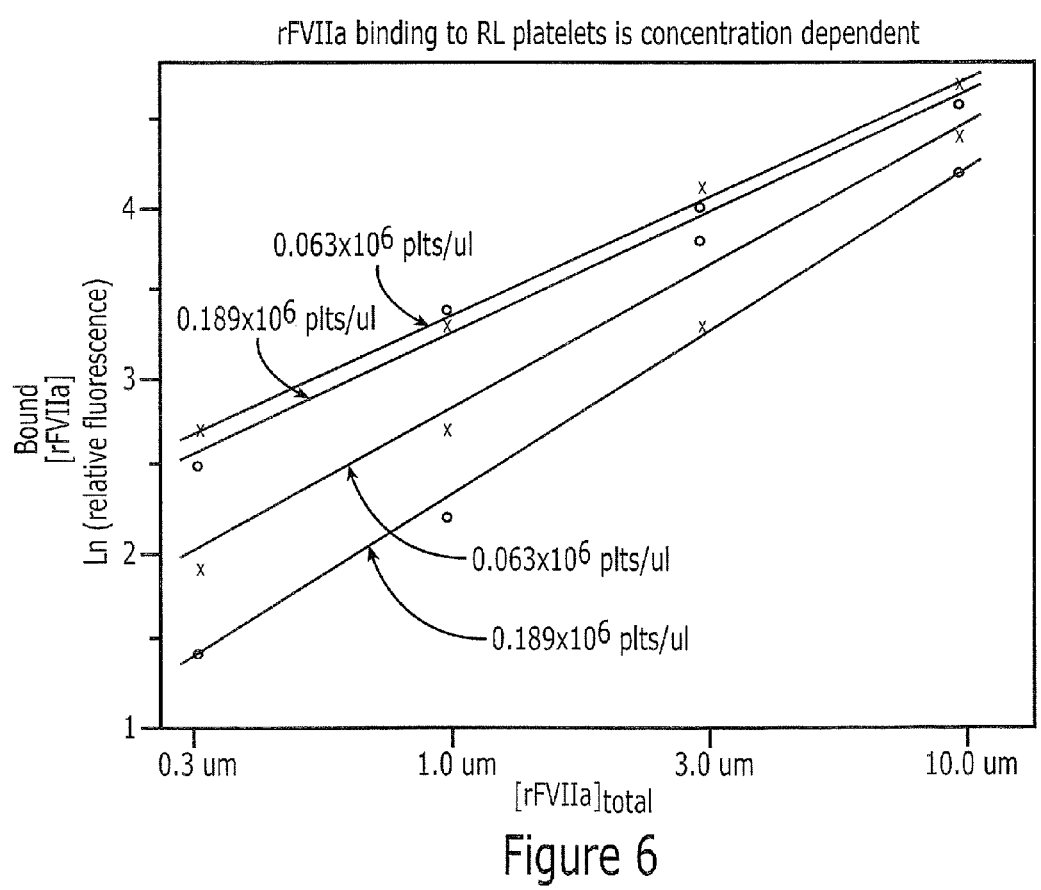
FIG. 6 shows that rFVIIa binding to RL:platelets is concentration dependent.

The degree of binding of rFVIIa-FITC to lyophilized platelets was an increasing function of total rFVIIa-FITC concentration (see FIG. 6, "rFVIIa binding to RL:platelets is concentration dependent").

These results show that significant amounts of rFVIIa can be attached to lyophilized platelets through simple co-incubation at super-physiological concentrations.

Figure 7:
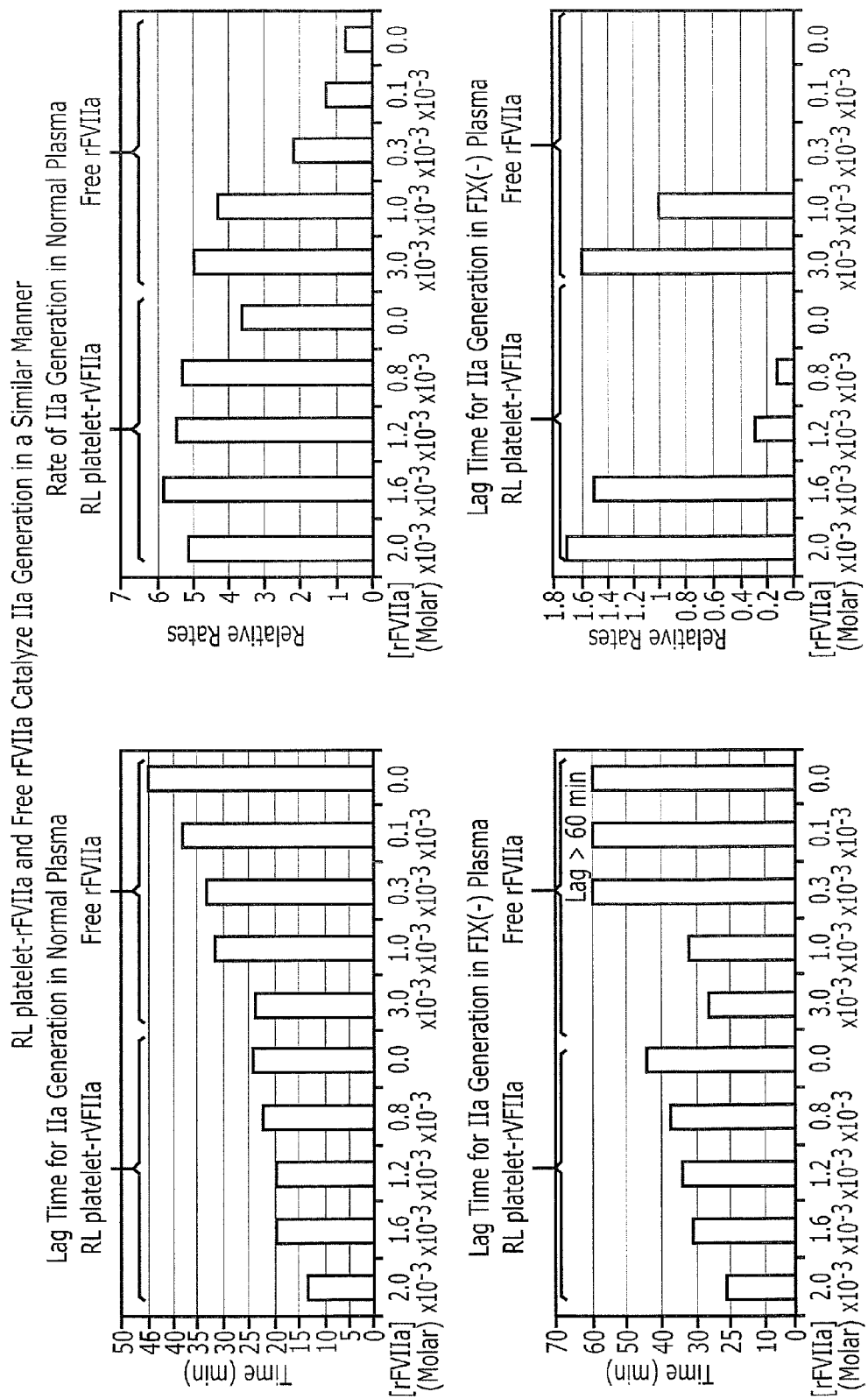
FIG. 7 shows that rFVIIa is active on the surface of RL platelets.

The activity of rFVIIa that is surface-bound to lyophilized platelets was analyzed by measuring the ability of these preparations to catalyze prothrombin to thrombin conversion. RL platelet-rFVIIa was prepared by incubating rFVIIa (10 uM, 3 uM, 1 uM 0.3 or 0 uM) with RL platelets ($1 \times 10^5$/ul) in citrated saline with 10 mM $CaCl_2$ for one hour. RL platelets-rFVIIa particles were centrifically washed once to remove unbound rFVIIa, then the preparations (as well as control buffer or similar concentrations of rFVIIa alone) were diluted 1/10 into normal or factor IX deficient plasma that contained the fluorometric thrombin substrate D-phe-pro-arg-ANSNH. The time for initiation and maximal rate of thrombin substrate generation was measured. The results in FIG. 7 show that RL platelet-bound rFVIIa is at least as active as free rFVIIa on a molar basis (See FIG. 7, "RL platelet-rFVIIa and free rFVIIa catalyze IIa generation in a similar manner".

References

Al Douri, M., Shafi, T., Al Khudairi, D., Al Bokhari, E., Black, L., Akinwale, N., Osman, M., Al Homaidhi, A., Al Fagih, M. and Borum, R. (2000) Effect of the administration of recombinant activated factor VII in the management of severe uncontrolled bleeding in patients undergoing heart valve replacement surgery. Blood Coag. and Fib. 11, S121-S127.

Arroyo, J., Jones, P., Porter, N. and Hatchell, D. (1997) In vivo photoactivation of caged thrombin. Thrombosis and Hemostasis 78, 791-793.

Artemov, D. (2003) Molecular magnetic resonance imaging with targeted contrast agents. J. Cellular Biochem. 90, 518-525.

Bode, A., Read, M., Reddick, R. (1999) Activation and adherence of lyophilized human platelets on canine vessel strips in the Baumgartner perfusion chamber. J. Lab. Clin. Med. 133, 200-211.

Carlsson. J., Drevin, H., and Axen, R. (1978) Protein thiolation and reversible protein-protein conjugation. Biochemistry J. 173, 723-737.

Chatterjee, J., Haik, Y. and Chen, C. (2003) Size dependent magnetic properties of iron oxide nanoparticles. J. Magnetism and Magnetic Materials 257, 113-118.

Chu, B., Wahl, G. and Orgel, L. (1983) Derivatization of unprotected polynucleotides. Nuc. Acids Rec. 11, 6513-6529.

Crotty, S., Cameron, C., Andino, R. (2002) Rivavirin's antiviral mechanism of action: Lethal mutagenesis? J. Mol. Med. 80, 86-95.

Di Stefano, G. and Fiume, L. (1997) Liver glycotargeting of antiviral nucleoside analogues. Trends in Glycosci. and Glycotech. 50, 461-472.

Dutton, R., Hess, J. and Scalea, T. (2003) Recombinant factor VIIa for control of hemorrhage: early experience in critically ill trauma patients. J. Clin. Aneth. 15, 184-188.

Fischer, T., Merricks, E., Russell, K., Raymer, R., White, G., Bode, A., Nichols, T. and Read, M. (2000) Intracellular Signaling in Rehydrated, Lyophilized Platelets. Brit. J. Haem. 111, 167-175.

Fischer, T., Merricks, E., Bellinger, D., Hayes, P. Smith, R., Raymer, R., Read, M., Nichols, T. and Bode, A. (2001a) Splenic clearance mechanisms of rehydrated, lyophilized platelets. Art. Cell. Blood Subs. 1 mm. Biotech. 29, 439-451.

Flacke, S., et al. (2001) Novel MRI contrast agent for molecular imaging of fibrin. Circulation 104, 1280-1285.

Fume et al., (1988) *Pharm. Acta. Helv.* 63, 137-139.

Hedner, U. and Glazer, S. (1992) Management of hemophilia patients with inhibitors. Hematology/Oncology Clinics of North America 6, 1035-1046.

Khandelwal, G., Sanders, W., Bode, A., Nichols, T., Erickson, G. and Read, M. (1997) von Willebrand factor binding to rehydrated lyophilized platelet surface GP1b and inhibition by monoclonal antibody to GP1b. FASEB J. 11, 1812.

Kristensen, J., Killander, A., Hippe, E., Helleberg, C., Ellegaard, J., Holm, H., Kutte, J., Mellqvist, U., Johansson, J., Glazer, S, and Hedner, U. (1996) Clinical experience with recombinant factor VIIa in patients with thrombocytopenia. Haemostasis 256, 159-164.

Monohan, P. and Samulski, J. (2000) Adeno-associated virus vectors for gene therapy: more pros than cons? (Mol. Med. Today 6, 433-440.

Monroe, D., Hoffman, M., Oliver, J. and Roberts, H. (1997) Platelet activity of high dose factor VIIa is independent of tissue factor. Br. J. Haematol. 99, 542-547.

Monroe, D., Hoffman, M., Allen, M. and Roberts, H. (2000) The factor VII-platelet interplay: Effectiveness of recombinant factor VIIa in the treatment of bleeding in severe thrombocytopenia. Seminars in Thrombosis and Hemostasis 26, 373-377.

Nichols, T., Bellinger, D., Davis, K., Koch, G., Reddick, R., Read, M., Rapacz, J., Hasler-Rapacz, J., Brinkhous, K., Griggs, T. (1992) Porcine von Willebrand disease and atherosclerosis: Influence of polymorphism in apolipoprotein B100 genotype. Am. J. Pathol. 140, 403-415.

Pankhurst, Q., Connolly, J., Jones, S, and Dobson, J. (2003) Applications of magnetic nanoparticles in biomedicine. J. Phys. D: Applied Phys. 36, R167-R181.

Poon, M. and d'Oiron, R. (2000) Recombinant activated factor VII treatment of platelet-related bleeding disorders. International Registry of recombinant factor VIIa and congenital platelet disorders group. Blood Coag. and Fib. 11, S55-S68.

Read M. S., Reddick R. L., Bode A. P., Bellinger D. A., Nichols T. C., Taylor K. K., Smith S. V., McMahon D. K., Griggs T. R., and Brinkhous K. M. (1995) Preservation of hemostatic and structural properties of rehydrated lyophilized platelets: Potential for long-term storage of dried platelets for transfusion. Proc. Natl. Acad. Sci. 92: 397-401.

Rofsky, N. and Adelman, M. (2000) MR angiography in the evaluation of atherosclerotic peripheral vascular disease. Radiology 214, 326-338.

Yoshikawa, M., Kato, T. and Takenishi, T. (1967) A novel method for phosphorylation of nucleosides to 5' nucleosides. Tetrahedron Lett 50, 5065-5068.

The foregoing is illustrative of the present invention, and is not to be construed as limiting thereof. The invention is defined by the following claims, with equivalents of the claims to be included therein.

That which is claimed is:

1. Aldehyde-fixed, dried, mammalian platelets carrying an exogenous active agent,
    wherein said exogenous active agent is selected from the group consisting of diagnostic agents and therapeutic agents and is covalently coupled to the interior of said aldehyde-fixed, dried, mammalian platelets, and
    wherein said aldehyde-fixed, dried, mammalian platelets, upon reconstitution, adhere to thrombogenic surfaces, undergo shape change upon adhering to a thrombogenic surface, and lead to the formation of a hemostatic plug upon adhering to a thrombogenic surface.

2. The aldehyde-fixed, dried, mammalian platelets of claim 1, wherein said aldehyde-fixed, dried, mammalian platelets comprise aldehyde-fixed, dried, human platelets.

3. The aldehyde-fixed, dried, mammalian platelets of claim 1, wherein, upon reconstitution, said aldehyde-fixed, dried mammalian platelets release their granular contents upon adhering to a thrombogenic surface.

4. The aldehyde-fixed, dried, mammalian platelets of claim 1, wherein said exogenous active agent comprises an antiviral agent.

5. The aldehyde-fixed, dried, mammalian platelets of claim 1, wherein said exogenous active agent comprises a blood coagulation protein.

6. The aldehyde-fixed, dried, mammalian platelets of claim 1, wherein said exogenous active agent comprises a blood anti-coagulation protein.

7. The aldehyde-fixed, dried, mammalian platelets of claim 1, wherein said exogenous active agent comprises a nucleic acid.

8. The aldehyde-fixed, dried, mammalian platelets of claim 1, wherein said exogenous active agent is selected from the group consisting of detectable compounds, antiviral agents, blood coagulation proteins, blood anti-coagulation protein, and nucleic acids.

9. The aldehyde-fixed, dried, mammalian platelets of claim 1, wherein said exogenous active agent is a detectable compound.

10. A pharmaceutical composition comprising:
    a pharmaceutically acceptable carrier; and
    aldehyde-fixed, dried, mammalian platelets having an exogenous active agent coupled thereto, said aldehyde-fixed, dried, mammalian platelets rehydrated in said pharmaceutically acceptable carrier,
        wherein said exogenous active agent is selected from the group consisting of diagnostic agents and therapeutic agents and is covalently coupled to the interior of said aldehyde-fixed, dried, mammalian platelets, and
        wherein said aldehyde-fixed, dried, mammalian platelets, upon reconstitution, adhere to thrombogenic surfaces, undergo shape change upon adhering to a thrombogenic surface, and lead to the formation of a hemostatic plug upon adhering to a thrombogenic surface.

11. The pharmaceutical composition of claim 10, wherein said carrier is a sterile carrier.

12. The pharmaceutical composition of claim 10, wherein said carrier is a solid carrier.

13. The pharmaceutical composition of claim 10, wherein said carrier is a liquid carrier.

14. The pharmaceutical composition of claim 10, wherein said carrier is an aqueous carrier.

15. The pharmaceutical composition of claim 10, wherein said aldehyde-fixed, dried, mammalian platelets comprise aldehyde-fixed, dried, human platelets.

16. The pharmaceutical composition of claim 10, wherein, upon reconstitution, said aldehyde-fixed, dried, mammalian platelets release their granular contents upon adhering to a thrombogenic surface.

17. The pharmaceutical composition of claim 10, wherein said exogenous active agent comprises an antiviral agent.

18. The pharmaceutical composition of claim 10, wherein said exogenous active agent comprises a blood coagulation protein.

19. The pharmaceutical composition of claim 10, wherein said exogenous active agent comprises a blood anti-coagulation protein.

20. The pharmaceutical composition of claim 10, wherein said exogenous active agent comprises a nucleic acid.

21. The pharmaceutical composition of claim 10, wherein said exogenous active agent is selected from the group consisting of detectable compounds, antiviral agents, blood coagulation proteins, blood anti-coagulation protein, and nucleic acids.

22. The pharmaceutical composition of claim 10, wherein said exogenous active agent is a detectable compound.

23. A method of making aldehyde-fixed, dried, mammalian platelets carrying an exogenous active agent, comprising:
providing aldehyde-fixed mammalian platelets;
coupling said exogenous active agent covalently to the interior of said aldehyde-fixed mammalian platelets; and
drying said aldehyde-fixed mammalian platelets to produce aldehyde-fixed, dried, mammalian platelets carrying said exogenous active agent;
wherein said exogenous active agent is selected from the group consisting of diagnostic agents and therapeutic agents, and
wherein said aldehyde-fixed, dried, mammalian platelets, upon reconstitution, adhere to thrombogenic surfaces, undergo shape change upon adhering to a thrombogenic surface, and lead to the formation of a hemostatic plug upon adhering to a thrombogenic surface.

24. The method of claim 23, wherein said aldehyde-fixed, dried, mammalian platelets carrying said exogenous active agent are rehydrated in a pharmaceutically acceptable carrier to provide a pharmaceutically acceptable composition comprising rehydrated aldehyde-fixed, dried, mammalian platelets carrying said exogenous active agent.

25. The method of claim 23, wherein said aldehyde-fixed mammalian platelets comprise aldehyde-fixed human platelets.

26. The method of claim 23, wherein, upon reconstitution, said rehydrated aldehyde-fixed, dried, mammalian platelets release their granular contents upon adhering to a thrombogenic surface.

27. The method according to claim 23, wherein said exogenous active agent is selected from the group consisting of detectable compounds, antiviral agents, blood coagulation proteins, blood anti-coagulation protein, and nucleic acids.

28. Aldehyde-fixed, dried, mammalian platelets carrying an exogenous active agent,
wherein said exogenous active agent is selected from the group consisting of diagnostic agents and therapeutic agents and is covalently coupled to the surface of said aldehyde-fixed, dried, mammalian platelets; and
wherein said aldehyde-fixed, dried, mammalian platelets, upon reconstitution, adhere to thrombogenic surfaces, undergo shape change upon adhering to a thrombogenic surface, and lead to the formation of a hemostatic plug upon adhering to a thrombogenic surface.

29. The aldehyde-fixed, dried, mammalian platelets of claim 28, wherein said aldehyde-fixed, dried mammalian blood cells comprise aldehyde-fixed, dried, human blood cells.

30. The aldehyde-fixed, dried, mammalian platelets of claim 28, wherein said aldehyde-fixed, dried, mammalian platelets, upon reconstitution, release their granular contents upon adhering to a thrombogenic surface.

31. The aldehyde-fixed, dried, mammalian platelets of claim 28, wherein said exogenous active agent comprises an antiviral agent.

32. The aldehyde-fixed, dried, mammalian platelets of claim 28, wherein said exogenous active agent comprises a blood coagulation protein.

33. The aldehyde-fixed, dried, mammalian platelets of claim 28, wherein said exogenous active agent comprises a blood anti-coagulation protein.

34. A pharmaceutical composition comprising:
a pharmaceutically acceptable carrier; and
the aldehyde-fixed, dried, mammalian platelets of claim 28, said aldehyde-fixed, dried, mammalian platelets rehydrated in said pharmaceutically acceptable carrier.

35. The pharmaceutical composition of claim 34, wherein said aldehyde-fixed, dried, mammalian platelets, upon reconstitution, release their granular contents upon adhering to a thrombogenic surface.

* * * * *